US009683975B2

(12) United States Patent
Sims

(10) Patent No.: US 9,683,975 B2
(45) Date of Patent: Jun. 20, 2017

(54) VOLUMETRIC FLOW REGULATION IN MULTI-DIMENSIONAL LIQUID ANALYSIS SYSTEMS

(71) Applicant: IDEX Health & Science LLC, Rohnert Park, CA (US)

(72) Inventor: Carl Sims, Santa Rosa, CA (US)

(73) Assignee: IDEX Health & Science LLC, Rohnert Park, CA (US)

( * ) Notice: Subject to any disclaimer, the term of this patent is extended or adjusted under 35 U.S.C. 154(b) by 59 days.

(21) Appl. No.: 14/620,924

(22) Filed: Feb. 12, 2015

(65) Prior Publication Data

US 2015/0226711 A1 Aug. 13, 2015

Related U.S. Application Data

(60) Provisional application No. 61/939,061, filed on Feb. 12, 2014.

(51) Int. Cl.
| | | |
|---|---|---|
| *G01N 30/32* | (2006.01) | |
| *B01D 15/08* | (2006.01) | |
| *B01D 15/42* | (2006.01) | |
| *G01N 30/20* | (2006.01) | |
| *G01N 30/46* | (2006.01) | |

(52) U.S. Cl.
CPC ............ *G01N 30/32* (2013.01); *B01D 15/08* (2013.01); *B01D 15/424* (2013.01); *G01N 30/20* (2013.01); *G01N 30/465* (2013.01); *G01N 2030/207* (2013.01); *G01N 2030/208* (2013.01); *G01N 2030/324* (2013.01)

(58) Field of Classification Search
CPC ....................................................... G01N 30/32
USPC ......................................................... 73/61.56
See application file for complete search history.

(56) References Cited

U.S. PATENT DOCUMENTS

| | | | |
|---|---|---|---|
| 3,645,142 A | 2/1972 | Turpin | |
| 4,300,393 A | 11/1981 | Stearns | |
| 5,255,568 A * | 10/1993 | del Valle | ............ G01N 35/1097 251/355 |

(Continued)

FOREIGN PATENT DOCUMENTS

| | | |
|---|---|---|
| EP | 495255 | 7/1992 |
| WO | 2010065138 | 6/2010 |
| WO | 2014015049 | 3/2014 |

OTHER PUBLICATIONS

Supplemental European Search Report and Search Opinion issued in related European patent application serial No. 13819301.6.

(Continued)

*Primary Examiner* — Michael A Lyons
*Assistant Examiner* — Jean Morello
(74) *Attorney, Agent, or Firm* — Haugen Law Firm PLLP

(57) ABSTRACT

A multi-dimensional liquid analysis system includes a first dimension system and a second dimension system, wherein outflow from the first dimension system is separated at a flow splitter under controlled conditions. The flow splitter separates the first dimension outflow into first and second split outlet flows, with one of the split outlet flows being metered to a designated flow rate with a flow metering device disposed downstream from the flow splitter. The flow metering device selectively closes or opens an outlet flow path to define a volumetric flow rate along that outlet flow path, so that the other split outlet flow is correspondingly controlled.

13 Claims, 8 Drawing Sheets

(56) References Cited

U.S. PATENT DOCUMENTS

| | | | |
|---|---|---|---|
| 5,305,982 | A | 4/1994 | Tamari |
| 5,607,581 | A | 3/1997 | Gerner et al. |
| 6,012,488 | A | 1/2000 | Nichols |
| 6,183,635 | B1 | 2/2001 | Klee et al. |
| 6,289,914 | B1 | 9/2001 | Tommasi |
| 6,453,725 | B1 | 9/2002 | Dahlgren |
| 6,730,228 | B2 | 5/2004 | Petro et al. |
| 6,802,967 | B2 | 10/2004 | Masuda et al. |
| 6,890,489 | B2 | 5/2005 | Nichols et al. |
| 7,132,650 | B1 | 11/2006 | Gamble et al. |
| 7,503,203 | B2 | 3/2009 | Gamache et al. |
| 7,575,723 | B2 | 8/2009 | Nichols et al. |
| 7,624,626 | B2 | 12/2009 | Lee |
| 7,900,504 | B2 | 3/2011 | Huynh et al. |
| 8,112,182 | B2 | 2/2012 | Tokuhisa et al. |
| 2002/0146349 | A1 | 10/2002 | Gygi et al. |
| 2003/0080062 | A1 | 5/2003 | Petro et al. |
| 2003/0159742 | A1 | 8/2003 | Karp et al. |
| 2005/0118075 | A1 | 6/2005 | Nichols et al. |
| 2005/0214130 | A1 | 9/2005 | Yang |
| 2006/0069418 | A1 | 3/2006 | Schock et al. |
| 2006/0157647 | A1 | 7/2006 | Sluzdak et al. |
| 2007/0199874 | A1 | 8/2007 | Ito et al. |
| 2008/0135484 | A1 | 6/2008 | Hammer |
| 2008/0314129 | A1 | 12/2008 | Schultz et al. |
| 2009/0090174 | A1 | 4/2009 | Paul et al. |
| 2010/0011888 | A1 | 1/2010 | Pawliszyn et al. |
| 2010/0288027 | A1 | 11/2010 | Ishii et al. |
| 2011/0247403 | A1 | 10/2011 | Liu |
| 2012/0240666 | A1 | 9/2012 | Sims et al. |
| 2013/0008859 | A1 | 1/2013 | Witt |
| 2014/0373605 | A1* | 12/2014 | Nichols .......... G01N 30/20 73/61.55 |

OTHER PUBLICATIONS

Kimura et al., "Simple 2D-HPLC Using a Monolithic Silica Column for Peptide Separation," J. Sep. Sci. 2004, 27, 897-904.

Motokawa et al., "Monolithic Silica Columns with Various Skeleton Sizes and Through-Pore Sizes for Capillary Liquid Chromatography," Journal of Chromatography A, 961 (2002) 53-63.

Tanaka et al., "Simple and Comprehensive Two-Dimensional Reversed-Phase HPLC Using Monolithic Silica Columns", Anal. Chem. 2004, 76, 1273-1281.

Search Report and Written Opinion in related International Application No. PCT/US2015/015643 dated May 18, 2015.

* cited by examiner

VOLUMETRIC FLOW REGULATION IN MULTI-DIMENSIONAL LIQUID ANALYSIS SYSTEMS

CROSS-REFERENCE TO RELATED APPLICATIONS

This application claims priority to U.S. Provisional Patent Application Ser. No. 61/939,061, filed on Feb. 12, 2014 and entitled "VOLUMETRIC FLOW REGULATION AND SAMPLE STREAM SPLITTING USING SHUTTLE STYLE SHEAR VALVES", the content of which being incorporated herein in its entirety.

FIELD OF THE INVENTION

The present invention relates to flow systems used in analytical chemistry, and more particularly to a splitting system for splitting mobile phase flow in a multi-dimensional liquid chromatography apparatus.

BACKGROUND OF THE INVENTION

A mixture of compounds, or analytes, can be separated by pumping the mixture through a separating device such as a chromatographic column using a process known as liquid chromatography, a variant of which is known as high performance liquid chromatography (HPLC). The separation of the sample is caused by analytes having different affinity for the chromatographic packing material within the column. The separated sample flows out of the chromatographic column continuously, but with the separated analytes emerging from the column at different times. The individual compounds comprising the analyte may then pass through various detection devices such as an ultraviolet light absorbance detector, a mass spectrometer, a fluorescence detector and the like to assist in determining the composition of the sample. The analytes may also be delivered to a receiver where each analyte might be stored in separate containers in a manner known as fraction collection. In some cases, a small amount of the column effluent may be directed to the inlet of another sample analysis device, such as a mass spectrometer to further analyze each individual analyte. The delivery of at least a portion of the column effluent to a further liquid analysis device is referred to as "second dimension" analysis, and is commonly employed in complex liquid analysis.

An example application for two dimensional liquid analyses is in the purification of a synthesized compound during the development of a new drug. Often, the products of the synthesis include the desired synthesized compound (with a known molecular weight), reactants and side products, all of which are analytes in the synthesis sample. In this example, a "first dimension" analysis carries out analytical or preparative scale separation, such as through an HPLC column, with a dedicated detection means such as a high flow rate refractive index detector or an ultraviolet light detector monitoring column effluent. A "second dimension" analysis may preferably utilize a second, separate flow path to capture a portion of the column effluent and direct the flow to a secondary analysis device, such as a mass spectrometer. Such combined instruments in a "two-dimensional" arrangement are becoming increasingly used to extend the understanding of the purity of compounds in a liquid scale.

For a second-dimension analysis device, such as a mass spectrometer, to function optimally, a controlled low mass rate of the eluent from the first dimension HPLC column containing the analyte should be delivered. Such mass or flow rates should be easily adjustable and closely controllable despite variations in the flow rate of the first dimension system. The flow rate should be reproducibly controlled, which facilitates second-dimension identification of the purity of an eluting peak of the desired synthesized compound to allow the collection of pure analyte in individual fractions. An experienced analyst may select a desired carrier fluid to transfer the analyte into the second-dimension detector, which second dimension carrier fluid may be different from the mobile phase used to perform the first-dimension preparative separation of the synthesized compound. Certain mobile phase fluids used to perform chromatographic separations may contain dissolved buffer salts which can cause fouling of a different second dimension analysis device such as a mass spectrometer, and certain organic components of the mobile phase can inhibit optimum ionization of the analytes which is required in a mass spectrometer. Proper selection of the carrier solvent reduces the effect on the mass spectrometer of the first-dimension analyte-mobile phase being transferred into the mass spectrometer. In addition, the analyte mass transfer rate into the mass spectrometer should be small, and generally should be a small fraction of the total analyte flow rate in the first dimension. A large mass rate to a mass spectrometer can result in a lingering or tailing signal that distorts the results of a mass spectrometer, and a large mass rate can change the dielectric properties of the system and cause a momentary loss of signal.

Analysts have, in some cases, attempted to operate combined HPLC and mass spectrometry instrumentation by reducing the HPLC mobile phase flow rate to a less than optimum value so that the outflow rate from the HPLC separation matches the liquid flow capacity of the mass spectrometer. Such reduction in flow rate through the HPLC column tends to reduce the available chromatographic resolution. To avoid the reduction in HPLC resolution, flow splitters have been employed in a full-flow regime to split a portion of the flow from the outlet of the HPLC column or detector to the inlet of the mass spectrometer, and the balance of the flow to another detector, or to waste. Typical commercial flow splitters make use of resistive tubing elements to split the liquid flow into two or more distinct flow streams. Example flow splitters are described in U.S. Pat. No. 6,289,914 and European Patent Application Publication No. EP495255A1. Resistive division of liquid flow is difficult to maintain at uniform levels. Factors such as variable viscosity of the mobile phase, temperature, and any variations in the flow path during the analysis may cause the split ratio between the respective flow paths to change. Such variability becomes of particular concern when multiple dimension liquid chromatography is practiced.

One example chromatographic application where mobile phase splitting is desirable is two-dimensional liquid chromatography (or LC*LC), wherein the first dimension HPLC column effluent is introduced into a second dimension HPLC column, with no portion of the first dimension separation not being introduced into the second dimension column for subsequent "second dimension" separation. Those of ordinary skill in the art of HPLC analysis understand the various techniques are known for injecting a sample into a chromatographic column. In many cases, a sample volume is established in a multi-port valve, and thereafter injected into the chromatographic column by a fluid force generated by a pump. Samples may be introduced into a flowing mobile phase stream.

Theoretically, it is desirable to have the entire volume of the first dimension separation injected into the second dimension separation column, though such an approach may be impractical as the rate of the effluent from the first separation column can be far too great to be directly injected into the second separation column. Traditionally, therefore, analysis of the "first dimension" separation has been accomplished by collection of the total volume of the effluent from the first separation column by fraction collection, and then re-injecting a representative sample of each fraction into the second dimension separation column.

In addition to flow rate mismatch, the developing chromatogram in the first dimension may contain increasing relative concentrations of organic solvent. The increasing relative concentration of organic solvent may be a result of the particular liquid chromatographic approach, in which an organic solvent is injected into the separation column after an aqueous mobile phase. As the relative concentration of organic solvent increases in the first dimension separation, injection of a fixed volume from the first dimension into the second dimension chromatograph further increases the relative organic solvent concentration during the second dimension separation. Under some conditions, injecting large volumes of organic solvent into the second dimension chromatograph is destructive to the second dimension separation. As the variation in organic solvent versus time occurs in the first dimension separation, the flow rate exiting from standard resistive flow splitters disposed downstream from the first separation column becomes unpredictable. Analysts therefore find it difficult to know the actual flow rate of sample available for injection into the second dimension separation column. An understanding of the sample flow rate is critical to control the organic solvent concentration in the second dimension separation column, and to ensure that no portion of the first dimension chromatograph is unsampled in the second dimension separation. Typical resistive flow splitters are not capable of providing analysts with the necessary information to consistently control analysis in the second dimension. Because of the limitations of standard resistive flow splitters, LC*LC has not enjoyed wide usage in the art.

A method for flow splitting using a negative displacement pumping scheme has been described in U.S. Patent Application Publication No. 2012/0240666A1. The method described in the '666 publication utilizes, for example, a syringe pump withdrawing a split flow from a flow splitter positioned upstream from a second-dimension injection valve. The volumetric flow rate of such split flow is determined by the negative displacement pump, acting to withdraw the split flow from the first dimension effluent at the flow splitter. Due to the compliance of the syringe pump under pressure, however, the withdrawal volume can vary widely depending upon the hydraulic stiffness of the syringe pump, the pressure applied, and the volume of the fluid under pressure in the negative displacement pump. A more consistent flow splitting scheme is therefore of interest to analysts, and is an object of the present invention.

SUMMARY OF THE INVENTION

By means of the present invention, split flows may be precisely controlled in a multi-dimensional liquid analysis system, in order to fulfil inlet flow rate requirements for second dimension analysis, while ensuring appropriate analysis of a representative sample of all of the first dimension effluent. Controlled flow splitting may be accomplished by directly exerting flow metering to one outlet stream from the flow splitter, thereby determining the flow output from the other outlet stream the flow splitter. The flow control may be performed by a valve establishing a discontinuity in an outlet flow path, wherein the discontinuity is bridged at desired time intervals. No additional unswept volume is interposed between the split point and any detection means attached to the uncontrolled leg of the flow splitter, such as a mass spectrometer).

In one embodiment, a multi-dimensional liquid analysis system includes a first dimension analysis system including a first separation column for chromatographically separating a liquid mobile phase into a first dimension outflow having a first dimension outflow rate. The system further includes a flow splitter for separating the first dimension outflow into a first split outlet flow and a second split outlet flow having a first pressure. A second dimension analysis system includes a second separation column for chromatographically separating the second split outlet flow into a second dimension outflow, and an injection valve for directing samples from the second split outlet flow into the second separation column. The injection valve includes an inlet port for receiving the second split outlet flow, an outlet port, and first and second discrete sample loops establishing flow channels alternately positionable into fluid communication with the second split outlet flow or the second separation column. The multi-dimensional liquid analysis system further includes a flow metering device for receiving the second split outlet flow from the outlet port of the injection valve along an outlet flow path. The flow metering device includes a valve for selectively closing or opening the outlet flow path in response to a control signal from a metering controller that is programmed to permit the second split outlet flow from the flow splitter at a predetermined second split outlet flow rate, as determined by a volume of the second split outlet flow permitted through the flow metering device along the outlet flow path within a designated period of time.

A method for analyzing a liquid sample includes pumping the liquid sample with a first pump to a first dimension analysis system having a first chromatographic column for identifying a chemical component of the liquid sample, wherein the first dimension analysis system yields a first dimension liquid outflow at a first dimension outflow rate. The method further includes separating the first dimension liquid outflow into a first split outlet flow and a second split outlet flow having a first pressure of at least one kilopascal, wherein the second split outlet flow is motivated by the first pump. The second split outlet flow is metered along an outlet flow path to a second split outlet flow rate by selectively closing or opening the outlet flow path with a flow metering device. The second split outlet flow is directed through a second dimension analysis system having a second chromatographic column for identifying the chemical component of the liquid sample. The second dimension analysis system includes an injection valve having an inlet port for receiving the second split outlet flow, an outlet port, and first and second discrete sample loops that form flow channels alternately positionable into fluid communication with the second split outlet flow or the second chromatographic column. Each of the first and second sample loops define respective first and second sample loop volumes, wherein the second split outlet flow rate is sufficient to permit the second split outlet flow to fill a respective one of the first and second sample loop volumes within a designated time period that is the sum of an analysis time and an equilibration time of the second chromatographic column.

DETAILED DESCRIPTION OF THE PREFERRED EMBODIMENTS

To effectuate consistent splitting of effluent flow from the first dimension analysis system, a flow metering device may be employed to selectively close or open a pressurized fluid flow path emanating from one outlet of a flow splitter device to thereby control the flow from such outlet to a designated rate. The resultant flow from a second outlet of the flow splitter is also therefore controlled. Such control dictates that the flow rate in both outlets of the flow splitter is known.

Figure 1:
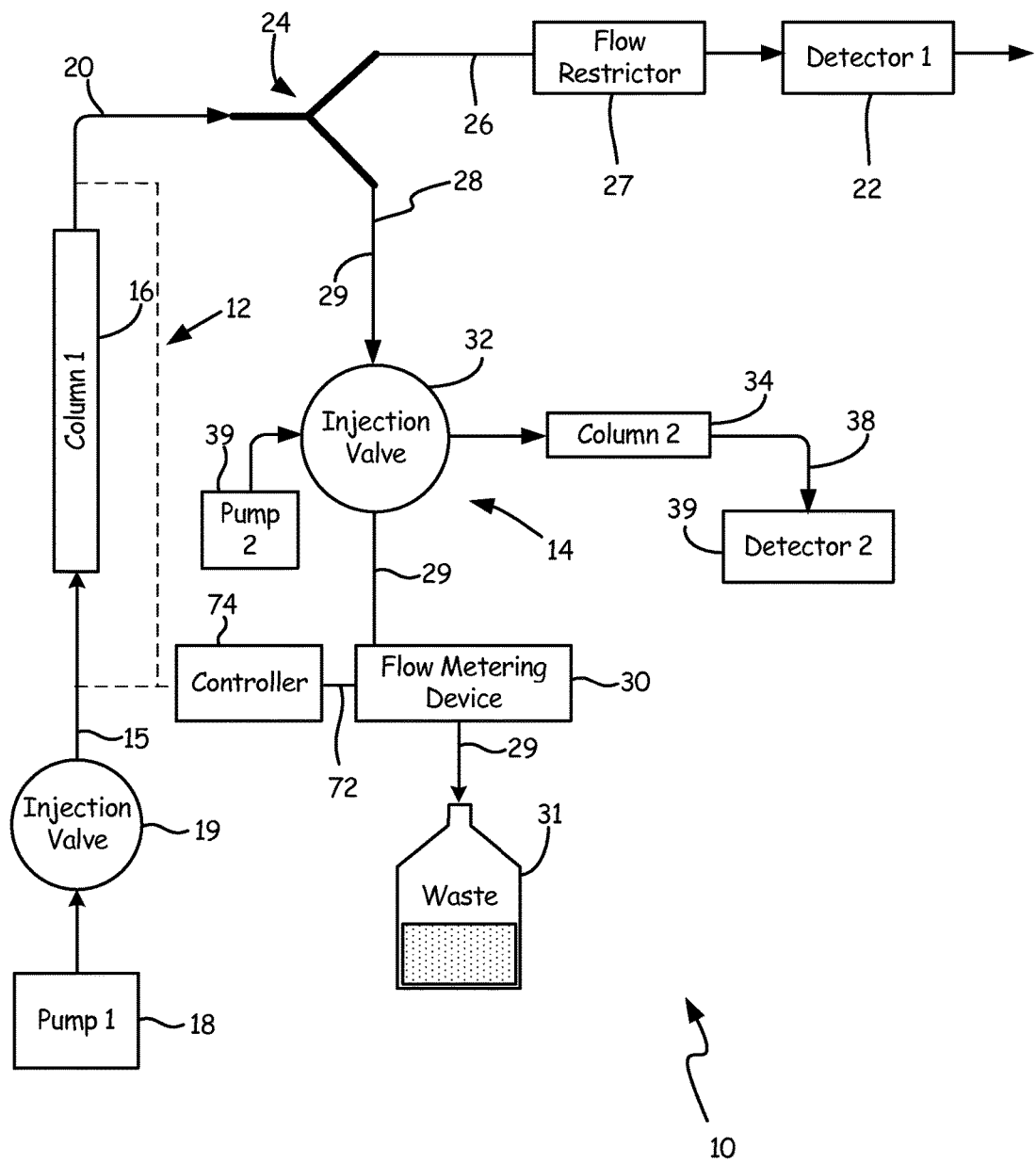
FIG. 1 is a schematic illustration of a multi-dimensional liquid analysis system of the present invention.

A first schematic diagram of an arrangement of the present invention is provided in FIG. 1. Multi-dimensional liquid analysis system 10 includes a first dimension analysis system 12, and a second dimension analysis system 14, wherein mobile phase is driven through a first dimension separation column 16 by first dimension pump 18, as driven through a first dimension injection valve 19. First separation column 16 chromatographically separates the liquid mobile phase into a first dimension outflow 20 having a first pressure and a first dimension outflow rate. First dimension outflow 20 may be delivered to a first dimension detector 22 directly, or may first be split by a flow splitter 24. The first dimension outflow rate into flow splitter 24 is controlled by first dimension pump 18, which defines the flow rate of mobile phase through first dimension separation column 16. First dimension pump 18 further defines the first pressure of first dimension outflow 20 downstream from first dimension separation column 16. The first pressure of first dimension outflow 20 is preferably at least one kilopascal, and is typically between 1-10,000 kilopascals. Preferably, the first pressure of first dimension outflow 20 is sufficient to establish a positive fluid pressure to both first dimension detector 22 and second dimension analysis system 14.

Flow splitter 24 may comprise a T-style junction fitting having a first inlet and first and second outlets, such as that available from Kinesis-USA as a "Micro-Splitter valve 10-32/6-32 Port 55 needle (EA)". In the arrangement illustrated in FIG. 1, a first split outlet flow 26 from flow splitter 24 may be directed to first dimension detector 22, and a second split outlet flow 28 from flow splitter 24 may be directed to second dimension analysis system 14 at a second pressure of between 1-10,000 kilopascals. To aid in maintaining the second pressure at a target point between 1-10,000 kilopascals, a flow restrictor 27 may be positioned to restrict first split outlet flow 26.

Analysis system 10 performs chemical analysis of a liquid sample pumped into first and second dimension columns 16, 34. For the purposes of this invention, first and second dimension "columns" may be construed broadly, so as to include analysis modalities that do not necessarily involve a column. For example, one or more of the dimensions may involve liquid chromatography, HPLC, preparative scale liquid chromatography, supercritical fluid analysis, gel permeation chromatography, mass spectrometry, other spectrometry or chromatography analysis, and combinations thereof. In a particular application, the first and second dimensions are each chromatographic columns for evaluating a liquid sample. In some embodiments, such liquid chromatography may be "high pressure liquid chromatography" or "high performance liquid chromatography" (HPLC), which is a common technique for performing chromatographic separations of solutions of compounds delivered to an injection valve or "autosampler" by pump for injection into the chromatographic separation column. Liquids and liquid mixtures used to transport the compounds are referred to herein as the "mobile phase". The "stationary phase" of liquid chromatography is typically the packing materials within the separation columns 16, 34.

Second dimension analysis system 14 includes second separation column 34 for chromatographically separating second split outlet flow 28 into a second dimension outflow 38 for analysis at a second dimension detector 39 which may comprise, for example, a mass spectrometer.

As indicated above, flow control may be applied to second split outlet flow 28 with a flow metering device 30 that is operable to selectively close or open outlet flow path 29 of second split outlet flow 28. Flow metering device 30 may operate in response to a control signal 72 from a metering controller 74 that is programmed to permit second split outlet flow 28 from flow splitter 24 at a predetermined second split outlet flow rate, as determined by a volume of second split outlet flow 28 permitted through flow metering device 30 along outlet flow path 29 within a designated period of time.

Metering controller 74 may receive data inputs, such as fluid pressure, flow rate, temperature, and the like from the first dimension flow stream, including first dimension outflow 20, and a first dimension inflow 15. Along with inputted system information, metering controller 74 may emit a control signal 72 for operating flow metering device 30 to open or close outlet flow path 29 at desired time intervals, to therefore regulate second split outlet flow rate over a designated period of time. In doing so, the operation of flow metering device 30 also controls a flow rate from first outlet 26 of flow splitter 24.

Flow metering device 30 may comprise a valve that is capable of selectively opening or closing outlet flow path 29 at desired time intervals. In some embodiments, flow metering device 30 may include a valve device that is capable of moving discrete liquid aliquot volumes across a flow path discontinuity. The movement of the discrete liquid aliquot volume represents "flow" of the volume along the flow path, or crossing a flow path discontinuity. Thus, flow metering device 30 receives and dispenses second split outlet flow 28 along outlet flow path 29, wherein flow metering device 30 constitutes a discontinuity in outlet flow path 29 that may be intermittently bridged by discrete liquid aliquot volumes. The rate at which the discontinuity in outlet flow path 29 is bridged by flow metering device 30, as well as the volume of each discrete liquid aliquot, determines the second split outlet flow rate permitted by flow metering device 30.

A variety of valve structures are contemplated as being useful as flow metering device 30. Some example conventional mechanisms for bridging a flow stream discontinuity by transferring a discrete liquid aliquot volume are described in U.S. Pat. Nos. 6,890,489 and 7,575,723, assigned to the same assignee as in this application, and incorporated herein by reference. A further example mechanism for flow metering device 30 is described in U.S. Patent Application Publication No. 2014/0373605A1, assigned to the same assignee as in this application, and incorporated herein by reference. In general, such a valve mechanism includes a shuttle for receiving a liquid aliquot of known volume from second split outlet flow 28 at an inlet station, and moving the liquid-filled shuttle across the discontinuity to a discharge station at which the liquid aliquot is discharged from the shuttle toward, for example, a waste receptacle 31. Flow metering device 30 accordingly moves the shuttle among at least two distinct shuttle stations for "flowing" discrete volumes of second split outlet flow 28 along outlet flow path 29 at a desired rate. In doing so, the flow rates of both first and second split outlet flows 26, 28 may be operably controlled. When the shuttle is not receiving second split outlet flow 28 at its inlet station, flow metering device 30 blocks second split outlet flow 28 upstream from flow metering device 30. The valve-limited flow rate of second split outlet flow 28, along with the fluid pressure of first dimension outlet flow 20, forces a known fluid flow rate through the first outlet leg of flow splitter 24 to first split outlet flow 26.

Figure 2A:
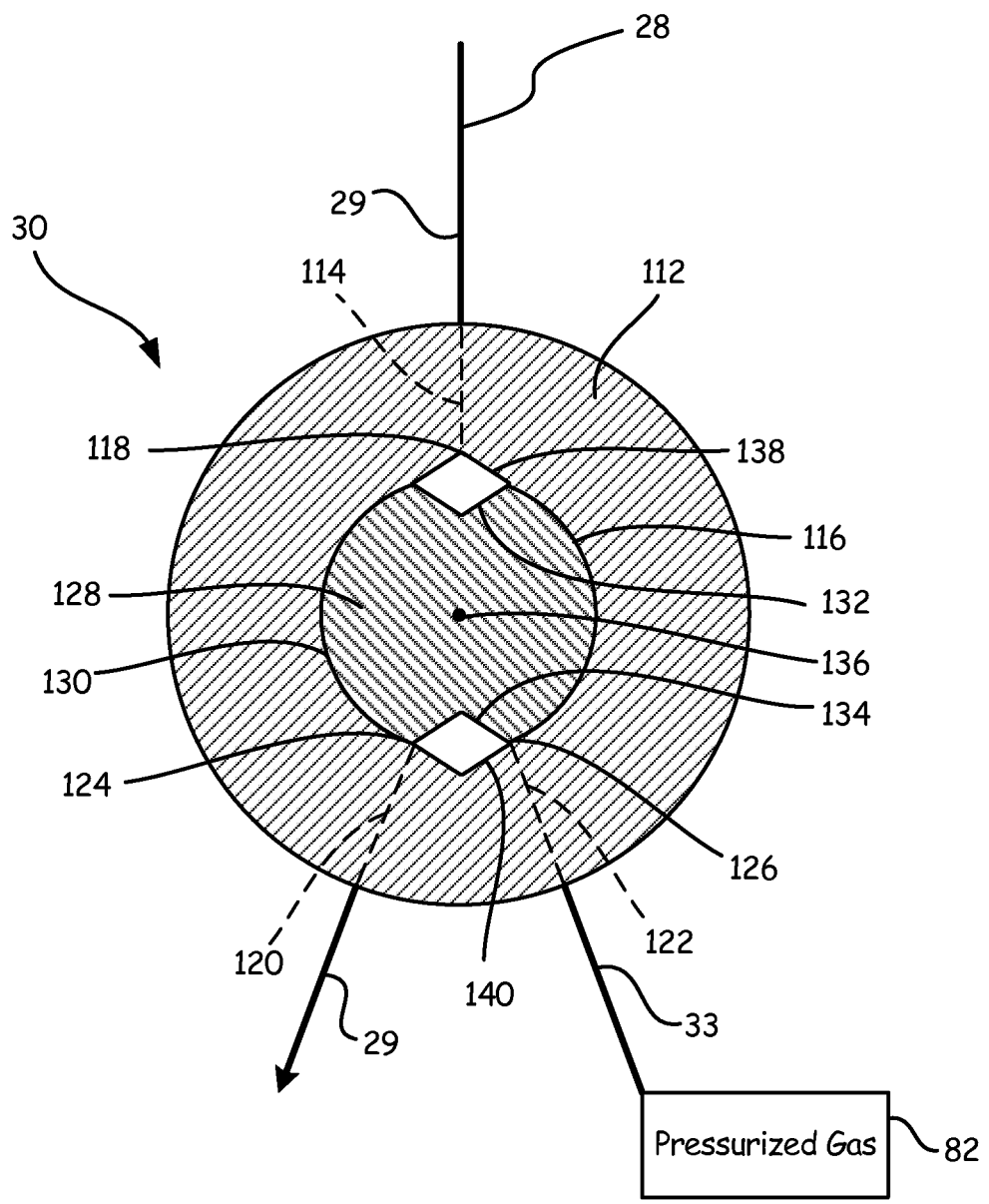
FIG. 2A is a schematic illustration of a flow metering device of the present invention.
Figure 2B:
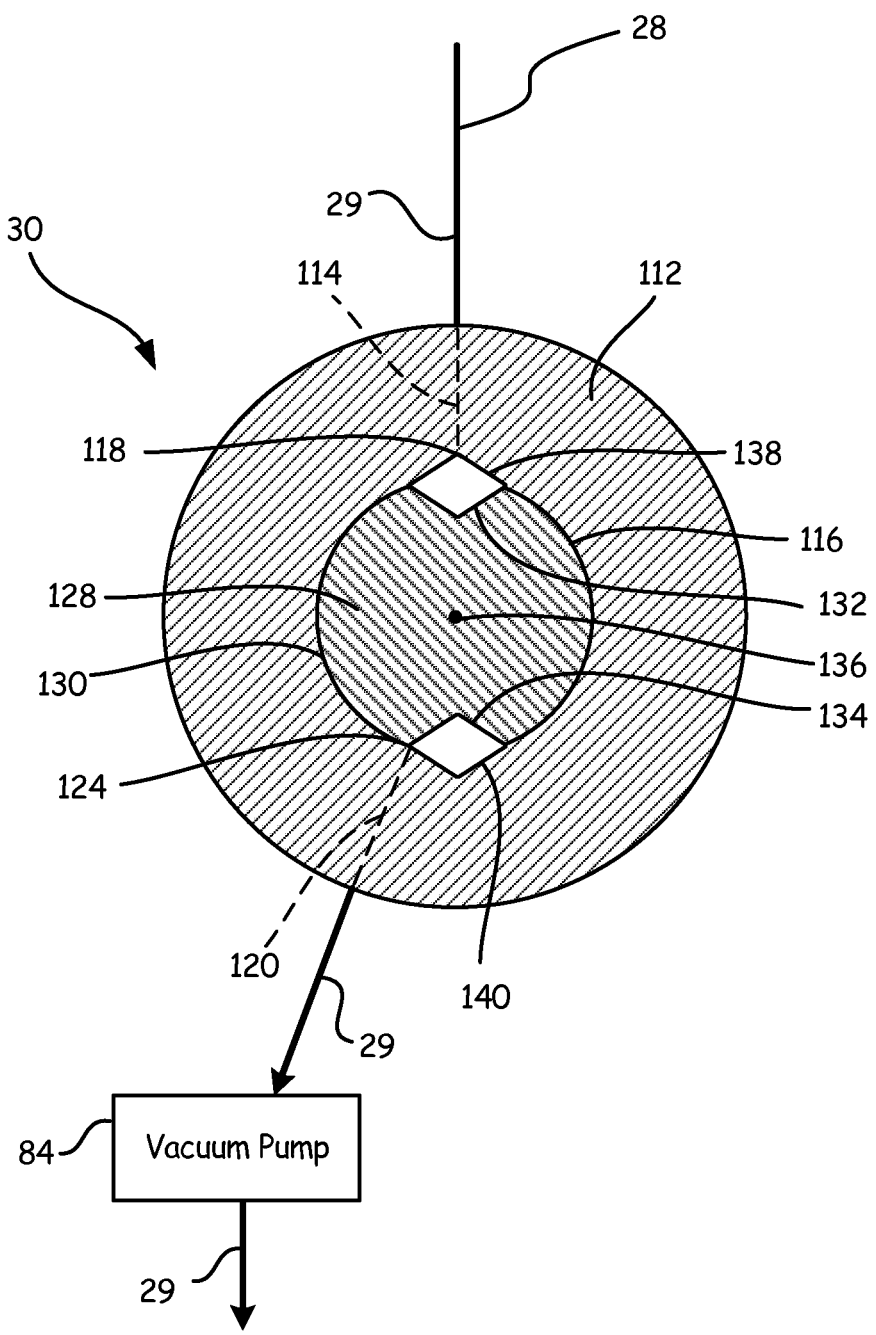
FIG. 2B is a schematic illustration of a flow metering device of the present invention.
Figure 3:
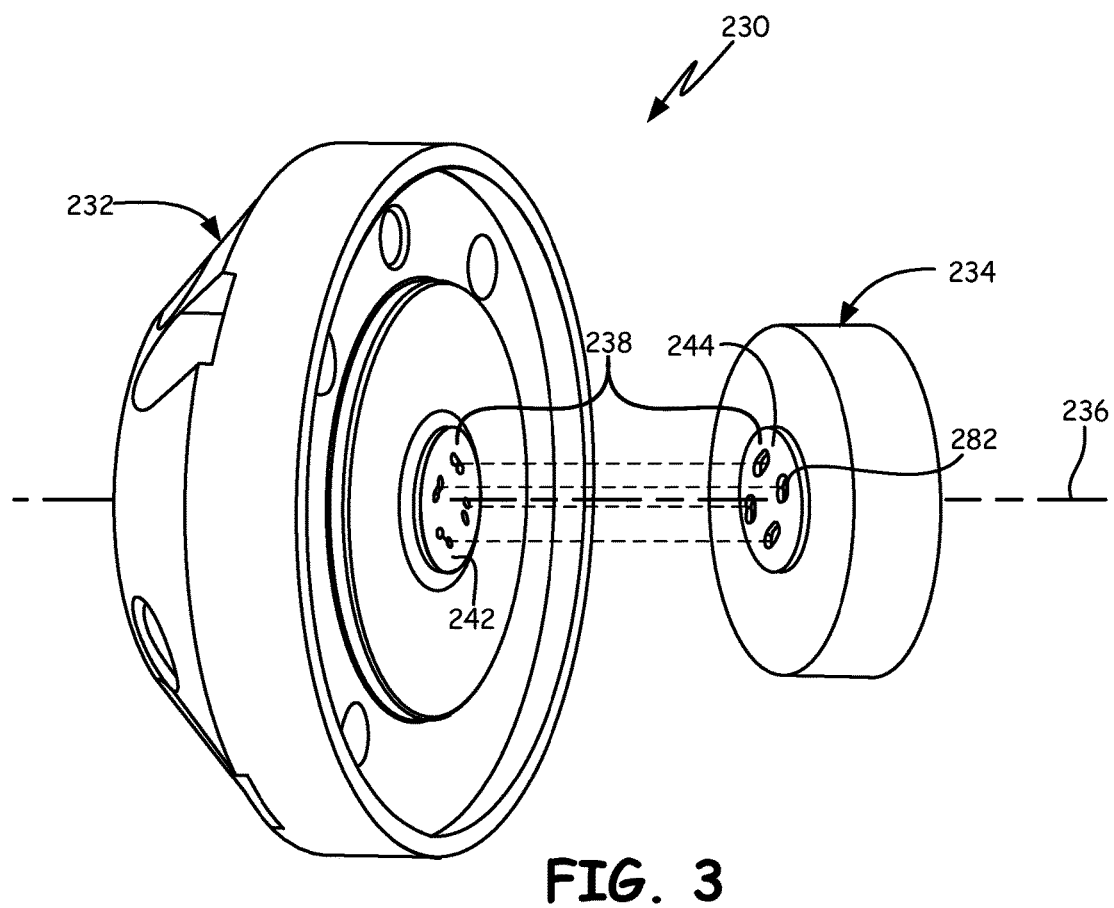
FIG. 3 is an exploded view of a portion of a flow metering device of the present invention.
Figure 4:
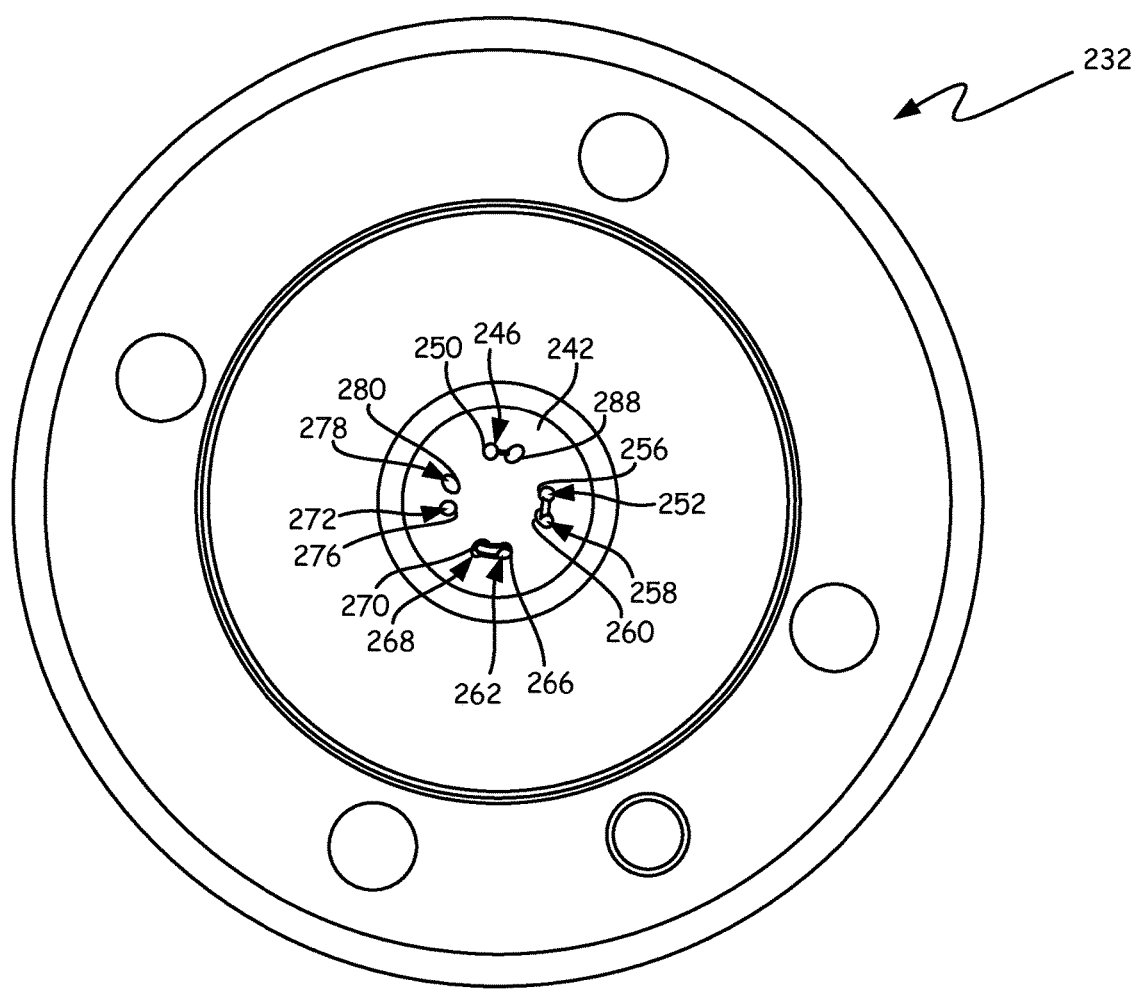
FIG. 4 is an isolation view of a portion of a flow metering device of the present invention.

A schematic illustration of an example embodiment for flow metering device 30 is illustrated in FIG. 2A. Flow metering device 30 includes a stator 112 having a first inlet stator passage 114 extending along outlet flow path 29 through stator 112, and opening to a stator face 116 through a first stator port 118. In the embodiment illustrated in FIG. 2A, stator 112 includes first and second discharge passages 120, 122, with the first discharge passage 120 extending along outlet flow path 29 through stator 112, and opening to stator face 116 through a second stator port 124 that is spaced from first stator port 118. The illustrated embodiment of flow metering device 30 further includes a rotor 128 having a rotor face 130 in fluid-tight contact with stator face 116 at an interface. Rotor face 130 includes a first shuttle 132 that is configured to receive a liquid aliquot in fluid communication with the interface. Rotor 128 is preferably rotatable with respect to stator 112 about an axis of rotation 136 to sequentially move first shuttle 132 into a plurality of circumaxially spaced stations, with a first station 138 aligning first shuttle 132 in fluid communication with outlet flow path 29 at first stator port 118. A second station 140 aligns first shuttle 132 in fluid communication with outlet flow path 29 at second stator port 124.

Flow metering device 30 may include a second shuttle 134 in rotor face 130 at a relative circumaxially spaced location at rotor face 130 such that, when first shuttle 132 is in fluid communication with outlet flow path 29 at first stator port 118, second shuttle 134 is positioned at second station 140 in fluid communication with outlet flow path 29 at second stator port 124. In such a manner, flow metering device 30 may be simultaneously receiving a second liquid aliquot from second split outlet flow 28 while a first, previously-received liquid aliquot may be discharged from second shuttle 134 through first discharge passage 120. It is contemplated that one or more shuttles may be provided at rotor face 130 to accommodate various second split outlet flow rate set points.

In some embodiments, flow metering device 30 may include second discharge passage 122 extending along a discharge path 33 through stator 112, and opening to stator face 116 through a third stator port 126. In this arrangement, second and third stator ports 124, 126 may be in fluid communication with each other at least when first or second shuttles 132, 134 are positioned at second station 140. Second discharge passage 122 may be provided to accommodate pressurized gas supplied through discharge path 33 from a pressurized gas source 82. The supply pressurized gas may act to displace the liquid aliquot from first or second shuttles 132, 134 when positioned at second station 140. Such displacement displaces the liquid aliquot out through second stator port 124, and through first discharge passage 120 along outlet flow path 29.

In another embodiment, second station 140 of rotor 128 may position first or second shuttles 132, 134 in fluid communication with second stator port 124 to discharge the liquid aliquot through first discharge passage 120 along outlet flow path 29. In order to effectuate discharge of the liquid aliquot from the respective first or second shuttles 132, 134, a reduced pressure may be applied through first discharge passage 120 by a vacuum pump 84. The vacuum force generated in outlet flow path 29 between second stator port 124 and vacuum pump 84 operably evacuates the liquid aliquot from first or second shuttles 132, 134 when positioned at second station 140. In some embodiments, application of a vacuum force to discharge the liquid aliquot from the respective shuttle may be preferred over other liquid aliquot discharge means, in that the reduced pressure environment left in the shuttle as it moves to first station 138 can aid in the filling of the shuttle with second split outlet flow 28 at first station 138. Namely, the reduced pressure in the shuttle creates a higher differential pressure ($\Delta p$) between second split outlet flow 28 and the "empty" volume of first or second shuttles 132, 134, with the increased $\Delta p$ assisting to drive second split outlet flow 28 into first or second shuttles 132, 134.

As described above, second split outlet flow 28 is permitted when a shuttle 132, 134 is positioned at first station 138. Typically, flow metering device 30 is programmed to permit a rotor dwell time at first station 138 and second station 140 that is sufficient to fill or discharge shuttles 132, 134, as appropriate. Upon the expiration of the rotor dwell time, metering controller 74 signals flow metering device 30 to rotate rotor 128 about axis 136 to bring first shuttle 132 to second station 140. During this transit period, rotor face 130 and stator face 116 are in fluid-tight contact, thereby closing outlet flow path 29. Once first shuttle 132 reaches second station 140, rotor 128 is again ceased for an appropriate fill/discharge time, during which period outlet flow path 29 is open, thereby permitting second split outlet flow 28. A flow cycle may be defined by the sum of the inlet/discharge rotor dwell period and the shuttle transit rotor rotation time period. The flow rate for second split outlet flow 28 is therefore determined by the shuttle volume and the flow cycle time. The rotor cycle time may be controlled to an extent by metering controller 74, but limited by operational limitations in rotor rotational speed, as well as fluid flow characteristics for liquid inlet and discharge, that are driven by $\Delta p$ at both first and second stations 138, 140, and liquid physical properties such as viscosity, surface tension, and the like. Upstream flow pressures may be measured and resultant data delivered to metering controller 74 so that flow metering device 30 may be operated at desired parameters to control the flow rates of both first and second split outlet flows 26, 28.

In the schematic arrangement illustrated in FIG. 1, flow metering device 30 is operably positioned downstream from a second dimension injection valve 32. It is to be understood, however, that flow metering device 30 may be operably positioned between flow splitter 24 and second dimension injection valve 32 along outlet flow path 29, such that the liquid aliquot discharged out through first discharge channel 120 is directed to second dimension injection valve 32. In such an embodiment, a flow metering discharge pump (not shown) pumping a second dimension mobile phase liquid from a liquid source pumps such liquid mobile phase through second discharge channel 122 to "carry out" the liquid aliquot of second split outflow 28 contained in the respective shuttle 132, 134 at second station 140, and out through first discharge channel 120 along outlet flow path 29. The second dimension mobile phase liquid could be the same or different from the first dimension mobile phase liquid. In order to accommodate re-filling of the shuttle 132, 134 with second split outlet flow 28 at first station 138, at least a third station is desired for evacuation or gas discharge of the second dimension mobile phase liquid pumped through the shuttle 132, 134 at second station 140.

An embodiment of flow metering device 30 including more than two rotor stations is illustrated in FIGS. 3-6, wherein flow metering device 230 includes a stator 232 and a rotor 234 that is rotatable with respect to stator 232 about an axis of rotation 236. Rotor 234 is mounted in flow metering device 230 in fluid-tight contact with stator 232 at an interface 238 so that fluid is permitted to pass between stator 232 and rotor 234 without leakage outside of flow metering device 230. Stator 232 includes a stator face 242 that is configured for sealing engagement with rotor face 244 of rotor 234. In some embodiments, stator face 242 and rotor face 244 may be substantially planar, and placed into sealing engagement with one another through an external mounting kit (not shown).

Stator 232 further includes an inlet stator passage 246 extending along outlet flow path 29 through stator 232 and opening to stator face 242 through first stator port 250. An inlet secondary stator passage 252 extends along a secondary path 254 through stator 232, and opens to stator face 242 through a second stator port 256. An outlet secondary stator passage 258 extends along secondary path 254 through stator 232, and opens to stator face 242 through a third stator port 260. An inlet discharge passage 262 extends along a discharge path 264 through stator 232, and opens to stator face 242 through a fourth stator port 266. An outlet discharge passage 268 extends along the discharge path 264 through stator 232, and opens to stator face 242 through a fifth stator port 270. In some embodiments, outlet discharge passage 268 extends along outlet flow path 29, as described above. In other embodiments, an inlet sweep passage 272 extends along a sweep path 272 through stator 232, and opens to stator face 242 through a sixth stator port 276. An outlet sweep passage 278 may extend along outlet flow path 29 through stator 232, and may open to stator face 242 through a seventh stator port 280.

The passages described above are fluidic passages that provide for the passage of fluids through stator 232. Such passages may be provided in sets, such as in groups of at least two, with an inlet passage and an outlet passage grouped for the conveyance of a respective fluid therethrough. It is contemplated, however, that at least inlet stator passage 246 may be provided in a set of at least one passage, wherein separate inlet and outlet passages for a particular fluid conveyance are not required.

The sets of fluidic passages coordinate with one or more shuttles 282 in rotor face 244 of rotor 234 to receive a liquid aliquot in fluid communication with interface 238. Rotor 234 is rotatable with respect to stator 232 about axis of rotation 236 to sequentially move shuttle 282 into a plurality of circumaxially spaced stations in fluid alignment with respective fluidic passage sets. A primary stator passage set 284 may include inlet stator passage 246, and optionally an outlet primary stator passage 286 that extends along an optional primary path 248 through stator 232 and opening to stator face 242 through an optional primary path port 288. In some embodiments, primary path 248 may be plugged to prevent undesired pass-through of second split outlet flow 28 through a shuttle 282 when in fluid communication with inlet stator passage 246.

A secondary stator passage set 290 includes inlet and outlet secondary stator passages 252, 258, and is preferably circumaxially spaced from primary stator passage set 284 at stator face 242. A discharge passage set 292 may include inlet and outlet discharge passages 262, 268, and may be circumaxially spaced from each of primary and secondary stator passage sets 284, 290 at stator face 242. A sweep passage set 294 may include inlet and outlet sweep passages 272, 278, and may be circumaxially spaced from each of primary stator passage set 284, secondary stator passage set 290, and discharge passage set 292 at stator face 242. The locations of each of passage sets 284, 290, 292, 294 may preferably define a station at stator face 242, wherein shuttle 282 may be moved with the rotation of rotor 234 from alignment from one station to the next. In some embodiments, rotor 234 is rotatable 360° about axis of rotation 236 so as to be sequentially brought into axial alignment with each of the stations defined by passage sets 284, 290, 292, 294 in stator face 242.

Figure 5:
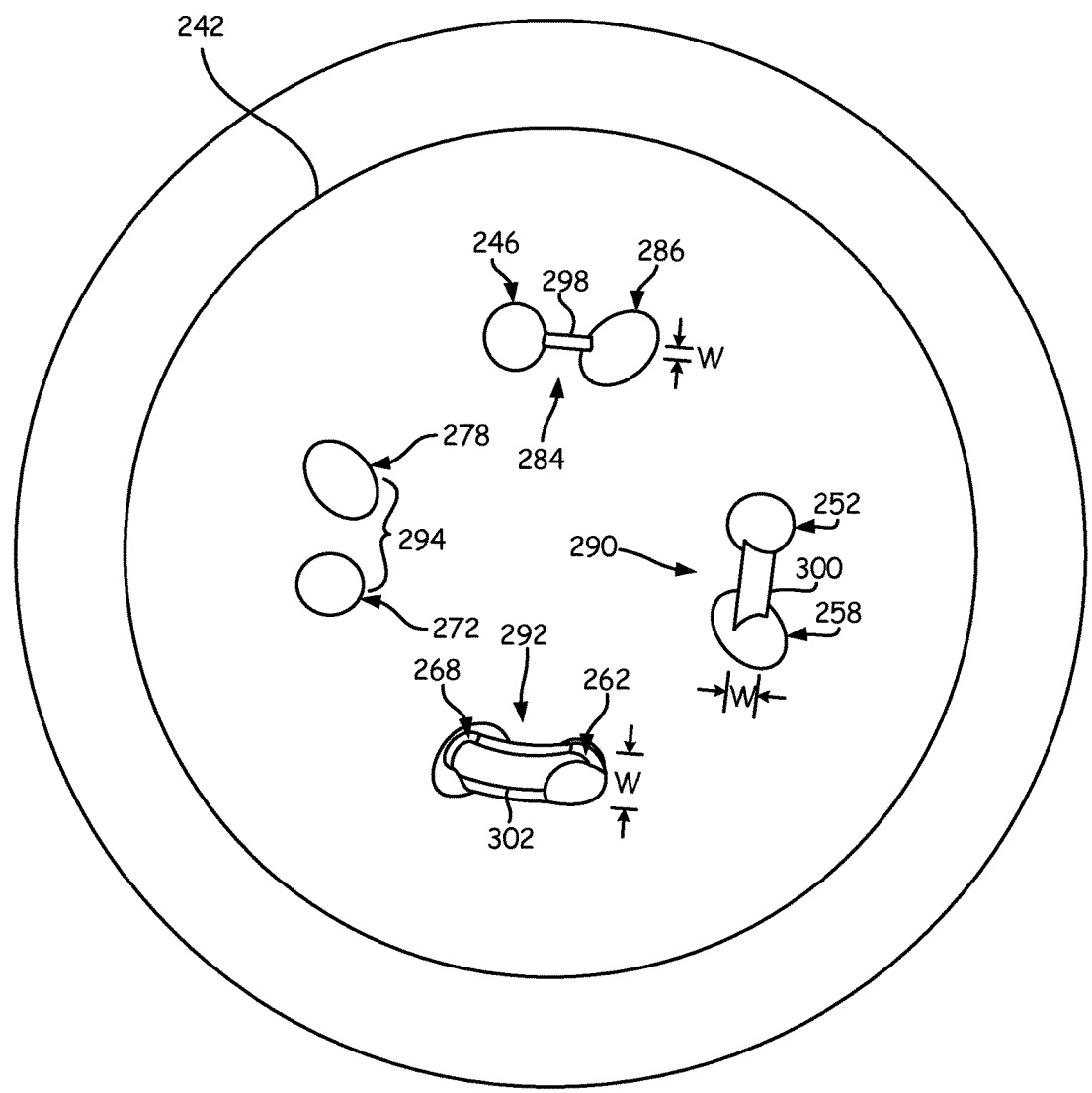
FIG. 5 is an isolation view of a portion of a flow metering device of the present invention.
Figure 6:
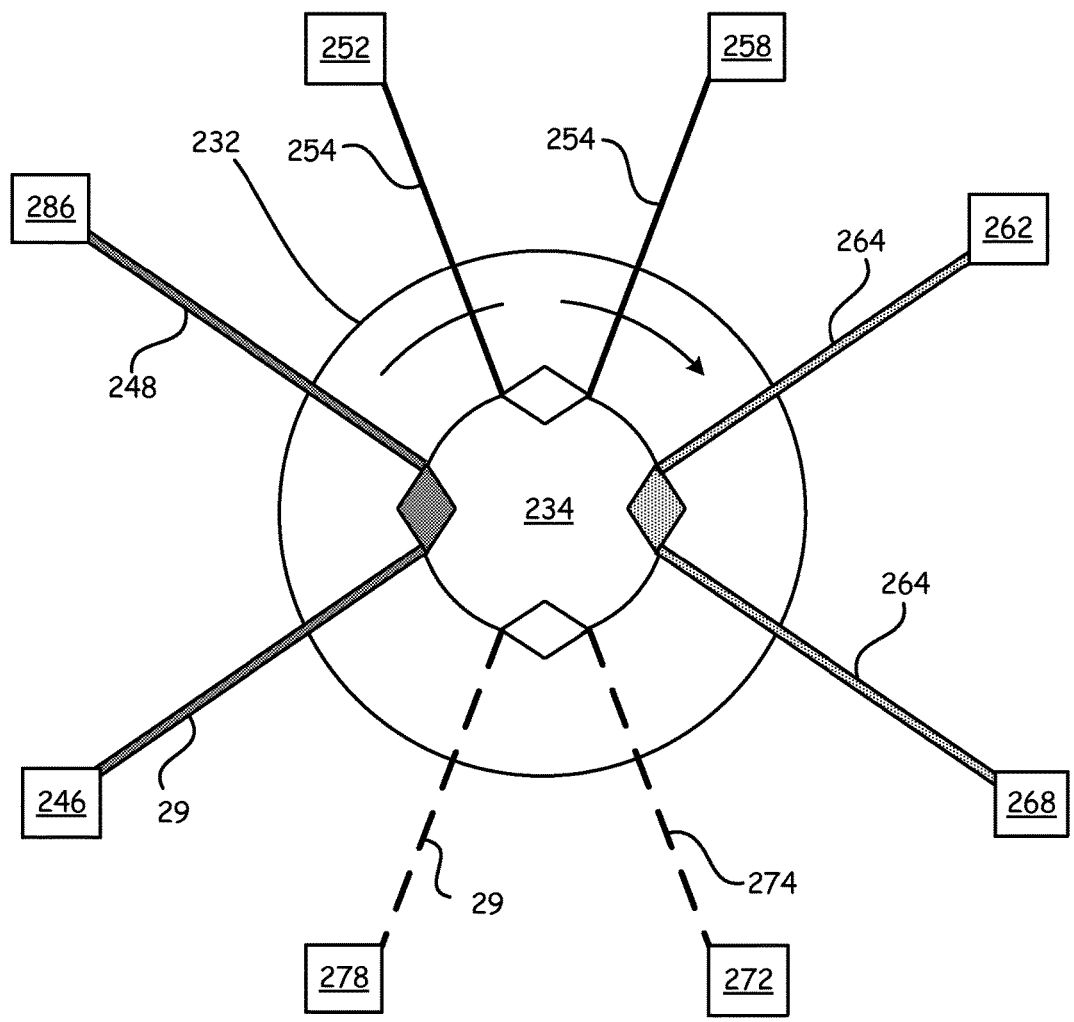
FIG. 6 is a schematic diagram of a flow metering device of the present invention.

In some embodiments of the invention, the respective fluid passages of one or more of passage sets 284, 290, 292, 294 may be fluidly connected to form a continuous fluid channel along the respective fluid path through stator 232 to interface 238 along a first leg, and then from interface 238 back through stator 232 along a second leg of the fluid path. Such a fluid connection among the fluidic passages in a given passage set permits continuous fluid flow along the respective fluid path when stator face 242 is sealed to rotor face 242, regardless of the circumaxial position of shuttle 282. When shuttle 282 is between stations on stator face 242, rotor face 244 acts as a block to fluid passage at interface 238. An example embodiment is illustrated in FIG. 5, wherein a primary bypass channel 298 is disposed in stator 232 to fluidly connect inlet stator passage 246 to outlet primary stator passage 286. A secondary bypass channel 300 is likewise provided in stator 232 to form a fluid connection between inlet and outlet secondary stator passages 252, 258. A discharge bypass channel 302 may be provided in stator 232 to form a fluid connection between inlet discharge passage 262 and outlet discharge passage 268. In the illustrated embodiment, no bypass channel is provided for sweep passage set 294. However, it is contemplated that a sweep bypass channel 304 may be included for sweep passage set 294 to establish a fluid connection in stator 232 between inlet and outlet sweep passages 272, 278. It is to be understood that any, all, or none of the fluid passages within any, all, or none of passage sets 284, 290, 292, 294 may have a fluid connection in stator 232, such as with respective bypass channels 298-304. The purpose of bypass channels 298-304, as described above, is to establish, in stator 232, a fluid connection among respective fluid passages. It is contemplated that bypass channels 298-304 may be of any appropriate size or configuration to suitably permit bypass fluid flow between respective fluid passages, and along a respective fluid path. Bypass channels 298-304 may, for example, be grooves in stator face 242 extending between respective ports of the fluid passages. In such an embodiment, the bypass channel may be open to interface 238, but enclosed by rotor face 244. In other embodiments, one or more of bypass channels 298-304 may be fully enclosed within stator 232. The channel widths "W" are shown in varying degrees in FIG. 5, representative of example widths relative to respective ports at stator face 242.

Shuttles 282 may be in the form of depressions in rotor face 244, and may be of equal or inequal volume. Example volumes defined within shuttles 282 may be between 10-1,000 nanoliters, with the shapes of shuttles 282 being appropriate to effectively receive and discharge liquid aliquots therefrom, as well as to establish and maintain desired fluid flow characteristics when positioned at a respective station in alignment with a corresponding fluid passage set 284, 290, 292, 294 of stator 232. It is contemplated that one or more of shuttles 282 may be provided in rotor face 244. The one or more shuttles 282 are movable with rotor 234 into a plurality of circumaxially spaced stations with the rotation of rotor 234 about axis of rotation 236. A first station aligns a shuttle 282 in fluid communication with outlet flow path 29 at first stator port 250. Rotating rotor 230 by a predetermined extent about axis of rotation 236 moves shuttle 282 to a second station aligning shuttle 282 in fluid communication with secondary path at second and third stator ports 256, 260. Further rotation of rotor 234 moves shuttle 282 to a third station aligning shuttle 282 in fluid communication with discharge path 264 at fourth and fifth stator ports 266, 270. In some embodiments, further rotation of rotor 264 moves shuttle 282 to a fourth station aligning shuttle 282 in fluid communication with sweep path 274 at sixth and seventh stator ports 276, 280. In some embodiments, each of the stations described above are separated by a 90° rotation about axis of rotation 236, such that rotor 234 is rotated 360° about axis of rotation 236 to cycle shuttle 282 through sequential alignment with respective passage sets 284, 290, 292, 294 at the circumaxially spaced stations. The cycle is repeatable through continued rotation about axis of rotation 236. Though just one shuttle 282 in rotor face 244 may fulfill the necessary functions of flow metering device 230, the desired rate for second split outlet flow 28 may be such that sufficient time may not exist for a single shuttle 282 to transit through each of the designated stations. In an example situation where one liquid aliquot per second is to be taken from second split outlet flow 28, a single shuttle 282 must be driven through each station in a total of one second, pausing at each station for a time sufficient to exchange the appropriate fluids. The limitations inherent therein may not permit a transfer across the flow path discontinuity of one sample per second from second split outlet flow 28 with only a single shuttle 282. The rate of rotation of rotor 232 can, however, be significantly reduced with the provision of additional shuttles 282. In the same example with a withdrawal interval of one sample per second, a rotor face 244 having four equally circumaxially spaced shuttles 282 could accomplish the desired sampling rate with a rotational rate of one revolution per four seconds (15 rpm). The significantly slower rotational rate of rotor 234 permits longer dwell times at each distinct shuttle station in the transfer cycle.

Figure 7A:
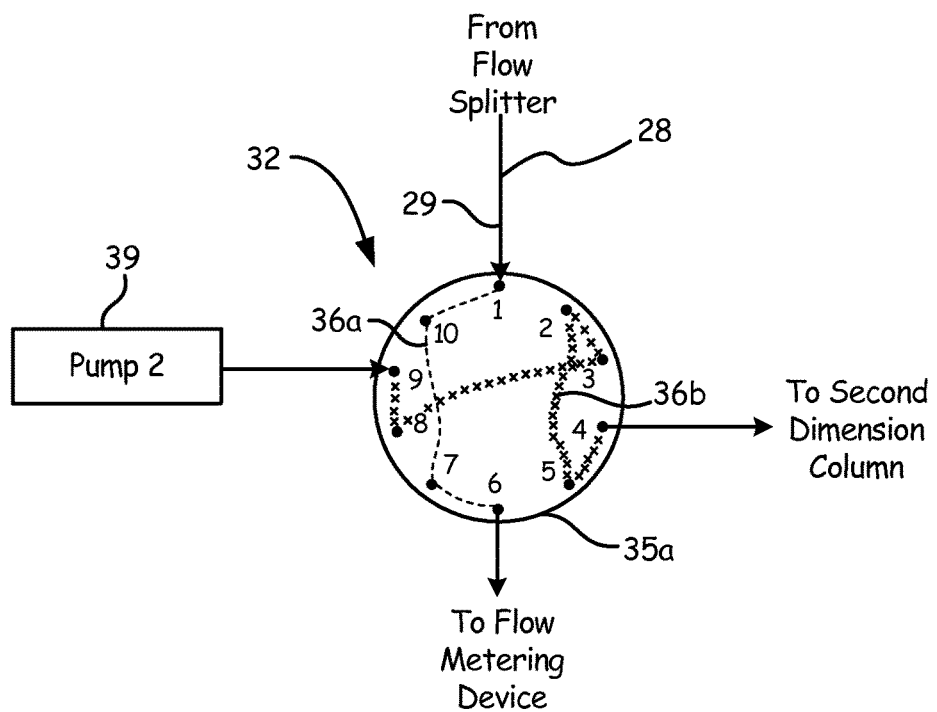
FIG. 7A is a schematic illustration of an injection valve of the present invention.
Figure 7B:
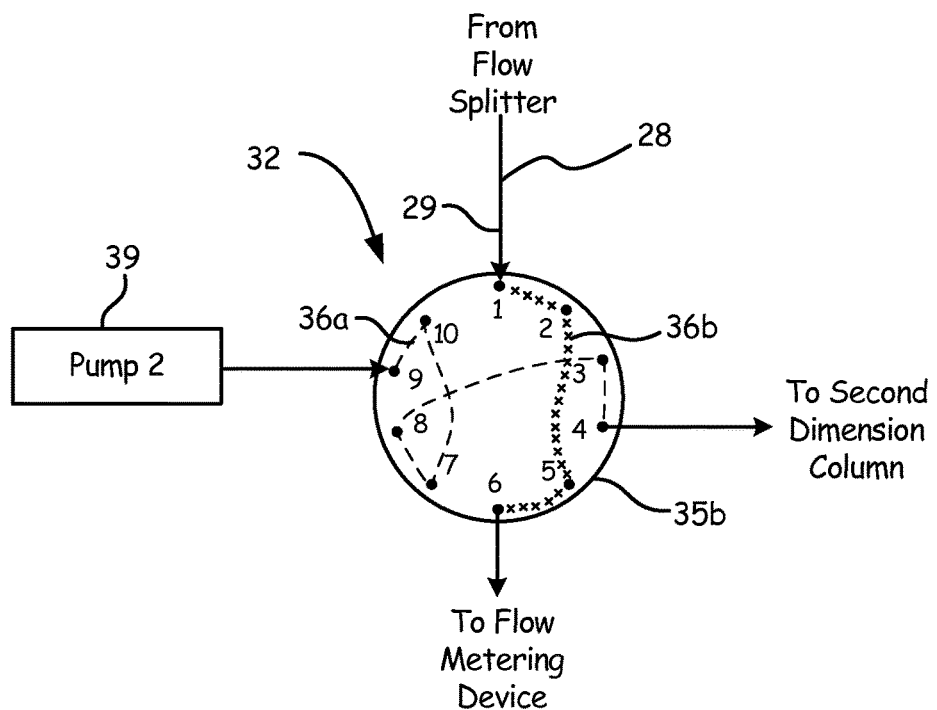
FIG. 7B is a schematic illustration of an injection valve of the present invention.

In some embodiments, second dimension injection valve 32 is a multiple port, multiple sample loop valve, as is known in the art. An example 10-port valve, as is known in the art, is illustrated in FIGS. 7A and 7B, representing second dimension injection valve 32 in first and second valve positions. In particular, second dimension injection valve 32 is illustrated in FIG. 7A in a first valve position 35a, wherein liquid from second split outlet flow 28, flowing along outlet flow path 29, is received at inlet port (1). Second dimension injection valve 32 may, in this embodiment, establish two distinct flow paths for use as a double loop injector. A first sample loop 36a comprises a flow channel extending between first sample loop ports (10, 7), wherein liquid is delivered from inlet port (1), and excess flows out from outlet port (6). In the first valve position 35a, first sample loop 36a is fluidly coupled to inlet port (1) and outlet port (6), while second sample loop 36b connects ports (2, 5), and is fluidly coupled to an injection pathway driven by second dimension pump 39 to second dimension column 34, via pump inlet port (9) through injection port (4), including ports (8, 3). Consequently, first sample loop 36a may be filled with second split outlet flow 28 while the sample within second sample loop 36b is analyzed in second dimension column 34.

Second dimension valve 32 is illustrated in a second position 35b in FIG. 7B, wherein second sample loop 36b may be filled while the sample within first sample loop 36a is analyzed in the second dimension column 34. In this case, second split outlet flow may be received at inlet port (1) at a flow rate controlled by flow metering device 30 to pass through second sample loop 36b at ports (2, 5), and out from second dimension injection valve 32 at outlet port (6). Injection of first sample loop 36a is driven by second dimension pump 39, sequentially through ports (9, 10, 7, 8, 3, 4). Flow of second split outlet flow 28 may be alternately directed into first or second sample loops 36a, 36b. The controlled flow rate of second split outlet flow 28 may be such that the sample loop volume being filled represents a volume suitable to be consumed over the entire time of the analysis and the equilibration of the second dimension analysis. First and second sample loops 36a, 36b may be alternately filled and injected to second dimension column 34. An advantage of this technique is that each sample loop 36a, 36b is fully washed by the mobile phase of the second dimension over the entire time of analysis to eliminate carryover. As described above, first sample loop 36a is in fluid communication with second separation column 34 when second sample loop 36b is in fluid communication with second split outlet flow 28.

In some embodiments, each of first and second sample loops 36a, 36b define respective first and second sample loop volumes that are equal to or greater than the desired sample volume deliverable to second dimension column 34. The permitted flow rate, as defined by flow metering device 30, may be substantially equal to such sample volume divided by the analysis time required of the second dimension column 34. In particular, the controlled flow rate is sufficient to permit second split outlet flow 28 to fill a respective one of the first and second sample loop volumes within a designated time period that is the sum of an analysis time and an equilibration time of second dimension column 34. Such calculated flow rate of second split outlet flow 28 ensures that a representative sample of all mobile phase passing through flow splitter 24 is delivered to second dimension column 34.

The following sets forth a relationship for an example control scheme for metering controller 74 to establish an appropriate flow rate for second split outlet flow 28 to ensure complete chromatographic analysis of the mobile phase in the second dimension column 34:

$$F_c \leq V_L/(T_{2a}+T_{2e})$$

Wherein,
$F_c$=controlled flow rate of second split outlet flow 28
$V_L$=volume of sample loop
$T_{2a}$=analysis time of second dimension column 34
$T_{2e}$=equilibration time of second dimension column 34

The "equilibration time" of the second dimension is the time required to "flush" the second dimension column of an opposite-phase solvent. For example, certain "HPLC" analyses are performed by first passing an aqueous phase through the column, followed by an organic phase, with the sample being injected as appropriate into one or both of the aqueous/organic phases. The sample is eluted through the chromatographic column through the sequence of alternating aqueous/organic phases. Once the sample has finished eluting through the chromatographic column, it is desired that the column be "cleared" of any remaining aqueous/organic phase that is opposite to the initial mobile phase in the subsequent sample analysis. Therefore, in the example of a sample tested with first an aqueous phase, followed by an organic phase, such organic phase is preferably "flushed" from the column with blank aqueous phase (such as water), prior to initiating the subsequent sample sequence. This "flushing" time is the "equilibration" time utilized in the above relationship.

The invention has been described herein in considerable detail in order to comply with the patent statutes, and to provide those skilled in the art with the information needed to apply the novel principles and to construct and use embodiments of the invention as required. However, it is to be understood that various modifications can be accomplished without departing from the scope of the invention itself.

What is claimed is:

1. A multi-dimensional liquid analysis system, comprising:
    a first dimension analysis system including a first separation column for chromatographically separating a liquid mobile phase into a first dimension outflow having a first dimension outflow rate;
    a flow splitter for separating said first dimension outflow into a first split outlet flow and a second split outlet flow having a first pressure;
    a second dimension analysis system including a second separation column for chromatographically separating said second split outlet flow into a second dimension outflow, and an injection valve for directing samples from said second split outlet flow into said second separation column, said injection valve having an inlet port for receiving said second split outlet flow, an outlet port, and first and second discrete sample loops comprising flow channels alternately positionable into fluid communication with said second split outlet flow or said second separation column; and
    a flow metering device for receiving said second split outlet flow from said outlet port of said injection valve along an outlet flow path, said flow metering device comprising a valve for selectively closing or opening said outlet flow path in response to a control signal from a metering controller that is programmed to permit said second split outlet flow from said flow splitter at a predetermined second split outlet flow rate, as determined by a volume of said second split outlet flow permitted through said flow metering device along said outlet flow path within a designated period of time, said valve having:
    (i) a stator having a stator face, a first inlet stator passage extending along said outlet flow path through said stator and opening to said stator face through a first stator port, a first discharge passage extending along said outlet flow path through said stator and opening to said stator face through a second stator port that is spaced from said first stator port, and a second discharge passage extending along a discharge path through said stator and opening to said stator face through a third stator port; and
    (ii) a rotor having a rotor face in fluid-tight contact with said stator face at an interface, said rotor face including a shuttle configured to receive a liquid aliquot in fluid communication with said interface, wherein said rotor is rotatable with respect to said stator about an axis of rotation to sequentially move said shuttle into a plurality of circumaxially spaced stations, a first station aligning said shuttle in fluid communication with said outlet flow path at said first stator port, and a second station aligning said shuttle in fluid communication with said outlet flow path at said second stator port wherein said second and third stator ports are in fluid communication with each other at least when said shuttle is positioned at said second station.

2. A multi-dimensional liquid analysis system as in claim 1, including a discharge means for discharging the liquid aliquot from said shuttle through said first discharge passage.

3. A multi-dimensional liquid analysis system as in claim 1 wherein said first and second sample loops each define respective first and second sample loop volumes that are each equal to or greater than an injection volume of said second split outlet flow needed for analysis by said second separation column.

4. A multi-dimensional liquid analysis system as in claim 1 wherein said first pressure is at least one kilopascal.

5. A multi-dimensional liquid analysis system as in claim 4 wherein said first pressure is between 1-10,000 kilopascals.

6. A multi-dimensional liquid analysis system as in claim 1 wherein said first sample flow channel is in fluid communication with said second separation column when said second sample flow channel is in fluid communication with said second split outlet flow.

7. A multi-dimensional liquid analysis system as in claim 1 wherein a first split outlet flow rate from said flow splitter is defined as the difference between said first dimension outflow rate and said second split outlet flow rate.

8. A method for analyzing a liquid sample, comprising:
    (a) pumping the liquid sample with a first pump to a first dimension analysis system for identifying a chemical component of the liquid sample, said first dimension analysis system yielding a first dimension liquid outflow at a first dimension outflow rate;
    (b) separating the first dimension liquid outflow into a first split outlet flow and a second split outlet flow having a first pressure of at least one kilopascal, wherein said second split outlet flow is motivated by said first pump;
    (c) metering said second split outlet flow along an outlet flow path to a second split outlet flow rate by selectively closing or opening said outlet flow path with a flow metering device, wherein said flow metering device includes
    (i) a stator having a stator face, a first inlet stator passage extending along said outlet flow path through said stator and opening to said stator face through a first stator port, a first discharge passage extending along said outlet flow path through said stator and opening to said stator face through a second stator port that is spaced from said first stator port, and a second discharge passage extending along a discharge path through said stator and opening to said stator face through a third stator port; and (ii) a rotor having a shuttle configured to receive a liquid aliquot, said rotor being movable to correspondingly move said shuttle to a plurality of spaced apart stations, a first station aligning said shuttle to receive the liquid aliquot from said second split outlet flow along said outlet flow path, and a second station aligning said shuttle to discharge the liquid aliquot to said second split outlet flow along said outlet flow path, wherein said second and third stator ports are in fluid communication with each other at least when said shuttle is positioned at said second station; and (d) directing said second split outlet flow through a second dimension analysis system having an analysis device for identifying a chemical component of the liquid sample, said second dimension analysis system including an injection valve having an inlet port for receiving said second split outlet flow, an outlet port, and first and second discrete sample loops comprising flow channels alternately positionable into fluid communication with said second split outlet flow or said analysis device, each of said first and second sample loops defining respective first and second sample loop volumes, wherein said second split outlet flow rate is sufficient to permit said second split outlet flow to fill a respective one of said first and second sample loop volumes within a designated time period that is the sum of an analysis time and an equilibration time of said analysis device.

9. A method as in claim 8 wherein said second split outlet flow is discontinuously connected at said flow metering device by said shuttle.

10. A method as in claim 8 wherein said outlet flow path is opened by positioning said shuttle at said first station.

11. A method as in claim 8, including directing said second split outlet flow from said outlet port of said injection valve to said flow metering device.

12. A method as in claim 8, including discharging the liquid aliquot from said shuttle by displacing the liquid aliquot with a gas.

13. A method as in claim 8, including displacing the liquid aliquot from said shuttle under an applied vacuum pressure.

* * * * *